(12) United States Patent
Luthra et al.

(10) Patent No.: US 8,835,442 B2
(45) Date of Patent: Sep. 16, 2014

(54) 3-SUBSTITUTED 7-IMINO-2-THIOXO-3, 7-DIHYDRO-2H-THIAZOLO [4,5-DI PYRIMIDIN-6-YL—AND PROCESS FOR PREPARATION THEREOF

(75) Inventors: Pratibha Mehta Luthra, Delhi (IN); Chandra Bhushan Mishra, Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 132 days.

(21) Appl. No.: 13/510,048

(22) PCT Filed: Nov. 3, 2010

(86) PCT No.: PCT/IN2010/000720
§ 371 (c)(1),
(2), (4) Date: Jun. 13, 2012

(87) PCT Pub. No.: WO2011/061754
PCT Pub. Date: May 26, 2011

(65) Prior Publication Data
US 2012/0264937 A1   Oct. 18, 2012

(30) Foreign Application Priority Data
Nov. 18, 2009   (IN) .......................... 2376/DEL/2009

(51) Int. Cl.
| | | |
|---|---|---|
| A01N 43/90 | (2006.01) | |
| A61K 31/519 | (2006.01) | |
| C07D 279/00 | (2006.01) | |
| C07D 471/00 | (2006.01) | |
| C07D 487/00 | (2006.01) | |
| C07D 491/00 | (2006.01) | |
| C07D 513/04 | (2006.01) | |

(52) U.S. Cl.
CPC .................................. *C07D 513/04* (2013.01)

USPC ....................................... 514/260.1; 544/255

(58) Field of Classification Search
None
See application file for complete search history.

(56) References Cited

U.S. PATENT DOCUMENTS
2006/0135526 A1   6/2006   Clasby et al.

FOREIGN PATENT DOCUMENTS
WO        99/51608 A1    10/1999
WO     2007/103776 A2     9/2007

OTHER PUBLICATIONS
Luthra, et. al., Bioorganic & Medicinal Chemistry Letters 20 (2010) 1214-1218.*

* cited by examiner

*Primary Examiner* — Jeffrey H Murray
(74) *Attorney, Agent, or Firm* — Ladas & Parry LLP

(57) ABSTRACT

The present invention relates to novel 3-substituted (7-imino-2-thioxo-3,7-dihydro-2H-thiazolo[4,5-d]pyrimidin-6-yl of formula 1 wherein R is selected from a group consisting of hydrogen, alkyl having carbon no up to 10, allyl, cycloalkyl, aromatic, substituted aromatics (halogen, OH, COOH, $OCH_3$, alkyl, etc), pyridyl, piperidine, piprazine, morphine. $R_1$ is selected from a group consisting of $NH_2$, NHR, $N(R)_2$ (wherein R could be aliphatic or olefinic group up to 10 carbon), hetrocycles such as furan, thiophene, pyrole, prydyl, piprazine, morphine and $R_2$ is O and S separately. Particularly the present invention relates to (7-Imino-3-substituted-2-thioxo-3,7-dihydro-2H-thiazolo[4,5-d]pyrimidin-6-yl)-urea (15-21) and Furan-2-carboxylic acid (7-imino-3-substituted-2-thioxo-3,7-dihydro-2H-thiazolo[4,5-d]pyrimidin-6-yl)-amide. The compounds of present invention are useful in the treatment of central nervous disorders including, Parkinson disease, Huntington's disease, attention disorder, cognition, Alzheimer disease, depression and hypertension.

10 Claims, No Drawings

3-SUBSTITUTED 7-IMINO-2-THIOXO-3, 7-DIHYDRO-2H-THIAZOLO [4,5-DI PYRIMIDIN-6-YL—AND PROCESS FOR PREPARATION THEREOF

RELATED APPLICATION INFORMATION

This application is a 371 of International Application PCT/IN2010/000720 filed 3 Nov. 2010 entitled "A Novel 3-Substituted 7-Imino-2-Thioxo 3,7-Dihydro-2H Thiazolo[4,5-Di Pyrimidin-6-YL And Process For Preparation Thereof", which was published in the English language on 26 May 2011, with International Publication Number WO 2011/061754 A1, and which claims priority from India Patent Application 2376/DEL/2009 filed 18 Nov. 2009, the content of which is incorporated herein by reference.

FIELD OF THE INVENTION

The present invention relates to novel 3-substituted (7-imino-2-thioxo-3,7-dihydro-2H-thiazolo[4,5-d]pyrimidin-6-yl. Particularly the present invention relates to (7-Imino-3-substituted-2-thioxo-3,7-dihydro-2H-thiazolo[4,5-d]pyrimidin-6-yl)-urea and Furan-2-carboxylic acid (7-imino-3-substituted-2-thioxo-3,7-dihydro-2H-thiazolo[4,5-d]pyrimidin-6-yl)-amide.

The compounds of present invention are useful in the treatment of central nervous disorders including, Parkinson disease, Huntington's disease, attention disorder, cognition, Alzheimer disease, depression and hypertension.

BACKGROUND OF THE INVENTION

Adenosine is an endogenous purine nucleoside that modulates a variety of physiological processes. At present, four adenosine receptor subtypes belonging to the family of G protein-coupled receptors (GPCRs) have been cloned and characterized ($A_1$, $A_{2A}$, $A_{2B}$, and $A_3$). Among four adenosine receptors, $A_{2A}$Receptors ($A_{2A}$Rs) appear to play the most important role in the control of motor behavior and in the modulation of dopamine-mediated responses (Pinna, A.; Wardas, J.; Simola, N.; Morelli, M.; *Life Sci.* 2005, 77, 3259-3267). These observations support therapeutic use of $A_{2A}$ antagonists for neurodegenerative disorders such as Parkinson's disease (PD) and Alzheimer's disease.

PD is a neurodegenerative disorder characterized by the loss of motor coordination manifested as tremor and rigidity of the limbs and trunk (Jenner, P.; *Neurology* 2003, 61, S32-S38). These symptoms are due to the deterioration and loss of dopaminergic neurons in the pars compacta region of the substantia nigra, which result in a decrease of dopamine in the striatum (Gillespie, et al. *Neurology* 2003, 61, 293-296.)

The finding revealed that the $A_{2A}$R is primarily located in the striatum and is co-expressed with the dopamine $D_2$ receptor which supports the role for $A_{2A}$ in motor activity (Shih-Jen, T. Medical hypotheses 2005, 64, 197-200). Results from different studies showed that $A_{2A}$Rs exert an excitatory influence on striatopallidal neurons, which is partially related to their antagonistic effect on dopamine $D_2$ receptor activation (Cieślak, M.; Komoszyńsk, M.; A Wojtczak Purinergic Signalling 2008, 4, 305-312) This functional interaction has suggested new therapeutic approaches for PD, based on the use of selective $A_{2A}$R antagonists. Therefore, antagonists of the $A_{2A}$ subtype of adenosine receptor have emerged as a leading candidate class of nondopaminergic antiparkinsonian agents (Kashe, H.; Biosci, Biotechnol, Bichem 2001, 65, 1447-1457). The effects of $A_{2A}$ antagonists have also been reported to afford neuroprotection in animal models of PD (Chen et al. Progress in Neurology, 2007, 83, 310-331)

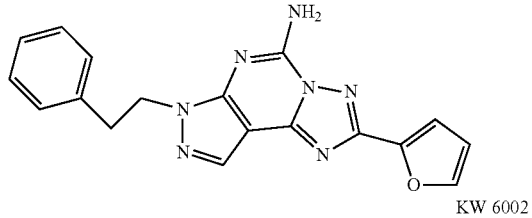

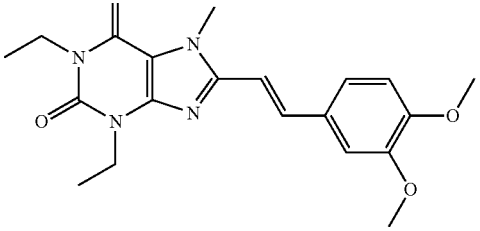

$A_{2A}$ antagonists SCH 58261 and KW 6002.

In the past ten years, great efforts have been devoted to identify potent and selective $A_{2A}$ adenosine antagonists. Recently, there has been much progress made in the discovery of small molecules as $A_{2A}$ antagonists and compounds such as KW-60021 has been the subject of clinical evaluation. These xanthine-based compounds have been reported to possess efficacy in models of the Parkinson's disease without inducing hyperactivity or inducing dyskinesias. (Kanda, T.; Jackson, M. J.; Smith, L. A.; Pearce, R. K. B.; Nakamura, J.; Kase, H.; Kuwana, Y.; Jenner, P. Exp. Neurol. 2000, 162, 321). More recently, the compound has been the subject of clinical evaluation, but failed to meet primary endpoints in two of the three essential trials (http://www.kyowa-kirin.co.jp/english/news/2009/e20090115_01.html). Additional non-xanthine compound such as SCH58261 have been reported and widely studied (Baraldi et al. J. Med. Chem. 2002, 45, 115) However, SCH 58261 suffered from several drawbacks including lower selectivity, poor solubility and pharmacokinetic profile.

In view of the limitation as described above for the use of known $A_{2A}$antagonist for the treatment of the central nervous system disorder such as Parkinson disease, there is need to develop novel compounds as $A_{2A}$ antagonist, free from the above said drawbacks.

Thiazoles have emerged as important class of compounds due to their antioxidant, anti-inflammatory, and neuro-protective effects (Hirota, T.; Leno, K.; Sasaki, K.; J. of Heterocyclic Chemistry, 1986, 23, 1685). A series of aryl/heteroaryl urea bearing thiazole moiety have emerged as a potent and selective inhibitors of cyclin dependent kinases for the treatment of Alzheimer's disease and other neurodegenerative disorders (Helal et al, Bioorg. Med. Chem. Lett. 2004, 14, 5521-5525).

Thiazolo[4,5-d]pyrimidine derivatives, which can be considered as thiole-analogues of the natural purine bases such as adenine and guanine, have acquired a growing importance in the field of medicinal chemistry because of their biological potential (Zhi, H.; Chen, L. M.; Zhang, L. L.; Liu, S. J.; Wan D. C. Cheong; Lin, H. Q.; Hu. C. ARKIVOC 2008 (xiii) 266-277). Furthermore, the recently demonstrated adenosine $A_{2A}$ receptor antagonistic activities of certain thiazoles with a urea moiety (Slee, D.; Lanier M.; Vong, B. G.; Chen, Y.; Zhang, X.; Lin. E.; Moorjani; M.; Castro, P.; Laria, J. C.; U.S. Pat. No. 20,080,275,064, 6 Nov. 2008) and thiazolopyrimidines (Sugihara, Y.; Kawakita, Y.; U.S. Pat. No. 20,080,269, 238, 30 Oct. 2008) for the development of a suitable approach to the treatment of PD.

In the present invention, novel thiazolo-pyrimidine pharmacophore was constructed with urea and furonamide moiety possessing aliphatic flexible groups, and aromatic planer structures as side chains as a potential $A_{2A}$ receptor antagonist.

OBJECTS OF THE INVENTION

The main objective of the invention is to provide novel (7-imino-2-thioxo-3,7-dihydro-2H-thiazolo[4,5-d]pyrimidin-6-yl—as potential Adenosine $A_{2A}$ Receptor antagonist.

Another object of the part of invention is to provide a process of preparation of (7-imino-2-thioxo-3,7-dihydro-2H-thiazolo[4,5-d]pyrimidin-6-yl—as potential Adenosine $A_{2A}$ Receptor antagonist.

Further object of invention is to provide a compound having better binding affinity, selectivity and antagonistic capability compared to known antagonist SCH58261 with adenosine $A_{2A}$ receptor.

SUMMARY OF THE INVENTION

Accordingly the present invention provides a novel compound of formula 1,

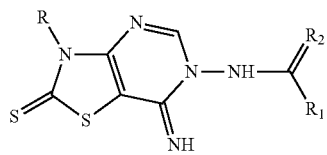

Formula 1 wherein R is selected from a group consisting of hydrogen; alkyl having carbon no up to 10, allyl, cycloalkyl, aromatic, substituted aromatics selected from the group consisting of halogen, OH, COOH, $OCH_3$, alkyl, pyridyl, piperidine, piprazine, morphine. $R_1$ is selected from a group consisting of $NH_2$, NHR, $N(R)_2$ (where R is aliphatic or olefinic group having up to 10 carbon), hetrocycles such as furan, thiophene, pyrole, prydyl, piprazine, morphine and $R_2$ is O or S separately.

In an embodiment of the present invention is disclosed the formula 1a comprising compounds No 15-21.

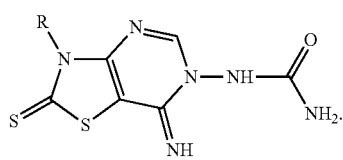

Formula 1a

Wherein R is selected from a group consisting of ethyl, propyl, allyl, butyl, phenyl, benzyl, and p-iodo phenyl.

In another embodiment of the present invention is disclosed the formula 1b comprising compound No 22-26

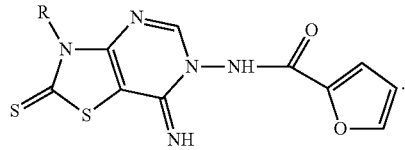

Formula 1b

Where R is selected from a group consisting of ethyl, propyl, allyl, butyl, and phenyl.

In still another embodiment of the present invention, is disclosed the representative compounds of formula 1 comprising;
a) (3-Ethyl-7-imino-2-thioxo-3,7-dihydro-2H-thiazolo[4,5-d]pyrimidin-6-yl)-urea. (15)
b) (7-Imino-3-propyl-2-thioxo-3,7-dihydro-2H-thiazolo[4,5-d]pyrimidin-6-yl)-urea (16)
c) (7-Imino-3-butyl-2-thioxo-3,7-dihydro-2H-thiazolo[4,5-d]pyrimidin-6-yl)-urea. (17)
d) (7-Imino-3-allyl-2-thioxo-3,7-dihydro-2H-thiazolo[4,5-d]pyrimidin-6-yl)-urea. (18)
e) (7-Imino-3-phenyl-2-thioxo-3,7-dihydro-2H-thiazolo[4,5-d]pyrimidin-6-yl)-urea. (19)
f) (3-p-iodophenyl-7-imino-2-thioxo-3,7-dihydro-2H-thiazolo[4,5-d]pyrimidin-6-yl)-urea (20)
g) (3-Benzyl-7-imino-2-thioxo-3,7-dihydro-2H-thiazolo[4,5-d]pyrimidin-6-yl)-urea (21)
h) Furan-2-carboxylic acid (3-ethyl-7-imino-2-thioxo-3,7-dihydro-2H-thiazolo[4,5-d]pyrimidin-6-yl)-amide. (22)
i) Furan-2-carboxylic acid (7-imino-3-propyl-2-thioxo-3,7-dihydro-2H-thiazolo[4,5-d]pyrimidin-6-yl)-amide (23)
j) Furan-2-carboxylic acid (3-butyl-7-imino-2-thioxo-3,7-dihydro-2H-thiazolo[4,5-d]pyrimidin-6-yl)-amide. (24)
k) Furan-2-carboxylic acid (7-imino-3-propenyl-2-thioxo-3,7-dihydro-2H-thiazolo[4,5-d]pyrimidin-6-yl)-amide. (25)
l) Furan-2-carboxylic acid (7-imino-3-phenyl-2-thioxo-3,7-dihydro-2H-thiazolo[4,5-d]pyrimidin-6-yl)-amide. (26)

In a further embodiment of the present invention are disclosed the compounds which are useful for the treatment of central nervous disorders including, Parkinson disease, Huntington's disease, attention disorder, cognition, Alzheimer disease, depression and hypertension.

In an embodiment of the present invention are disclosed the compound which showed Adenosine $A_{2A}$ receptor affinity ranges (0.0038-1.2 nM) which is better than the standard antagonist SCH58261 (1.23 nM)

In an embodiment of the present invention is disclosed the compounds which show Adenosine $A_{2A}$ receptor antagonistic ability in the range of 0.048-0.14 nM c AMP concentration) which is better than the standard antagonist SCH58261 (0.25 nM).

Accordingly the present invention provides a process for preparation of novel 3-substituted (7-imino-2-thioxo-3,7-dihydro-2H-thiazolo[4,5-d]pyrimidin-6-yl-amide wherein the process steps comprising
a) reacting imino ether derivatives of formula A

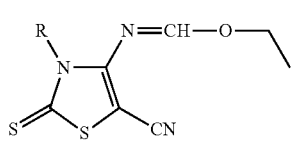

A wherein R is selected from a group consisting of, ethyl, propyl, allyl, butyl, phenyl, benzyl, and p-iodo phenyl with acid hydrazide in alcoholic solvent in presence of basic catalyst selected from a group consisting of amine, KOH, NaOH, at a temperature ranging between 20-3° C. for a period ranging between 6-12 hrs to obtain precipitated compound, b) filtering the precipitated compound as obtained in step (a) and followed by washing with ethanol/water to obtain the desired compound of formula 1.

In an embodiment of the present invention, the acid hydrazide is selected for the group consisting of semicarbazide, furoic acid hydazide, thiophene-2-carboxylic acid hydrazide, benzoic acid hydrazide, iso-nicotinic acid hydrazide, pyrimidine-4-carboxylic acid hydrazide, triazole-4-carboxylic acid hydrazide.

In another embodiment of the present invention, the alcoholic solvent used is selected from a group consisting of ethanol, methanol, propanol, iso-propanol, butanol, and mixture thereof

DETAILED DESCRIPTION OF THE INVENTION

Novel bicyclic thiazolopyrimide compounds containing urea and furonamide group were synthesized as adenosine $A_{2A}$ receptor ($A_{2A}R$) antagonists (scheme 1). Their binding affinities with $A_{2A}R$ have been evaluated using radioligand-binding assay on isolated membranes from stably transfected HEK 293 cells. Selectivity of the compounds towards $A_{2A}R$ was assessed by comparing their binding affinities with $A_1$ receptors ($A_1R$). Functional antagonism activity was confirmed by performing cAMP assay in HEK cell. The result revealed that the compounds having good $A_{2A}$ antagonistic property as compared to known $A_{2A}$ antagonist SCH58261 and said compound might be useful in various central nervous system disorder.

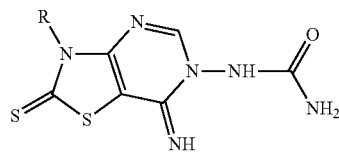

Structure of Designed and Synthesized Compounds

Synthesis of compound 1-14 has been carried out according to the procedure as disclosed and claimed in Patent Application No. 890/DEL/2009. Synthesis of novel designed compound 15-26 was carried according to scheme 1 described below.

Scheme 1

15-21
R = Ethyl, Propyl, Butyl, Allyl, Benzyl, Phenyl, p-iodophenyl 22-26
R = Ethyl, Propyl, Butyl, Allyl, Phenyl Reagents and conditions: (A) triethyl amine, RT; (B) triethyl orthoformate, PTSA, reflux; (C) Furoic acid hydrazide, triethyl amine, 25-30° C. and (D) semi-carbazide HCl, triethyl amine, RT.

The following examples are given by way of illustration and should not construed to limit the scope of the present invention.

EXAMPLE 1

Synthesis of (3-Ethyl-7-imino-2-thioxo-3,7-dihydro-2H-thiazolo[4,5-d]pyrimidin-6-yl)-urea (15)

A mixture of 4-(Ethoxymethylene)-amino-3-(ethyl)-2-thioxo-1,3-thiazole-5-carbonitrile 8 (5 g, 22.84 mmol), semicarbazide hydrochloride (2.6 g, 22.84 mmol) and triethyl amine (11 ml) in absolute ethanol (60 ml) was stirred at 20° C. for 12 hrs. The appeared precipitate was filtered and washed with absolute ethanol (36 ml) and water (38 ml) to give pure target compound 15 (4 g) and purity of compound was confirmed by HPLC.

Yield: 85%. (HPLC purity 100%), White solid; mp: 212° C. IR (KBr), 3248, 3164 ($NH_2$), 2958, 2781 (alkyl), 1674 (C=O). $cm^{-1}$ $^1H$ NMR ($DMSOd_6$): δ 1.25 (t, 3H, J=6.6 Hz, $CH_3$), 4.26 (q, 2H, J=6.6 Hz, $CH_2$), 6.59 (s, 2H, $NH_2$), 8.19 (s, 1H, N=CH), 9.24 (br, 1H, NH) $^{13}C$ NMR ($DMSOd_6$): δ 12.3, 40.7, 105.5, 115.5, 157.9, 159, 186.5. LC-MS: m/z 270 ($M^+$).

EXAMPLE 2

Synthesis of 7-Imino-3-propyl-2-thioxo-3,7-dihydro-2H-thiazolo[4,5-d]pyrimidin-6-yl)-urea (16)

A mixture of 4-(Ethoxymethylene)-amino-3-(-propyl)-2-thioxo-1,3-thiazole-5-carbonitrile 9 (6 g, 24.7 mmol), semicarbazide hydrochloride (2.8 g, 24.7 mmol) and triethyl amine (12 ml) in absolute ethanol (75 ml) were stirred at 25° C. for 12 hrs. The appeared precipitate was filtered and washed with absolute ethanol (35 ml) and water (34 ml) to give pure target compound 16 (5.2 g) and purity of compound was confirmed by HPLC.

Yield: 86%. (HPLC purity 100%) White solid; mp: 220° C. IR (KBr), 3249, 3163 ($NH_2$), 2957, 2782 (alkyl), 1673 (C=O) $cm^{-1}$. $^1H$ NMR (DMSO): δ 0.89 (t, 3H, J=7.2, $CH_3$), 9.70 (s, 1H, NH), 1.67-1.79 (m, 2H, CH2), 4.28 (t, 2H, J=7.2 Hz, $CH_2$), 6.35 (s, 2H, $NH_2$), 8.40 (s, 1H, N=CH), 9.70 (s, 1H, NH) $^{13}C$ NMR (DMSO): δ 10.9, 20.2, 46.3, 98, 154, 155.8, 158.5, 159, 190.3.

EXAMPLE 3

Synthesis of (7-Imino-3-butyl-2-thioxo-3,7-dihydro-2H-thiazolo[4,5-d]pyrimidin-6-yl)-urea (17)

A mixture of 4-(Ethoxymethylene)-amino-3-(butyl)-2-thioxo-1,3-thiazole-5-carbonitrile 10 (4 g, 15.6 mmol), semicarbazide hydrochloride (1.715.6 mmol) and triethyl amine (8 ml) in absolute ethanol (45 ml) was stirred at 25° C. for 14 hrs. The appeared precipitate was filtered and washed with absolute ethanol (50 ml) and water (45 ml) to give pure target compound 17 (3.5 g) and purity of compound was confirmed By HPLC.

Yield: 89%, (HPLC purity 100%), White solid; mp: 222° C. IR (KBr), 3246, 3163 ($NH_2$), 2955, 2780 (alkyl), 1675 (C=O). $cm^{-1}$. $^1H$ NMR (DMSO): δ 0.90 (t, 3H, J=7.2, $CH_3$), 1.26-1.38 (m, 2H, $CH_2$), 1.64-1.74 (m, 2H, $CH_2$), 4.31 (t, 2H, J=7.2 Hz, $CH_2$), 6.34 (s, 2H, $NH_2$), 8.34 (s, 1H, N=CH), 9.70 (s, 1H, NH) $^{13}C$ NMR (DMSO): δ 14, 19.9, 28.9, 45.1, 98.5, 156.3, 158.7, 159, 159.7, 190.7 LC-MS: m/z 298 ($M^+$), 299 ($M^{+1}$)

EXAMPLE 4

Synthesis of 7-Imino-3-allyl-2-thioxo-3,7-dihydro-2H-thiazolo[4,5-d]pyrimidin-6-yl)-urea (18)

A mixture of 4-(Ethoxymethylene)-amino-3-(allyl)-2-thioxo-1,3-thiazole-5-carbonitrile 11 (12 g, 49.8 mmol), semicarbazide hydrochloride (5.5 g, 49.8 mmol) and triethyl amine (25 ml) in absolute ethanol (105 ml) were stirred at 28° C. for 13 hrs. The appeared precipitate was filtered and washed with absolute ethanol (80 ml) and water (60 ml) to give pure target compound. 18 (10 g) and purity of compound was confirmed by HPLC.

Yield: 90%. (HPLC purity 99.5%), White solid; mp: 202° C. IR (KBr), 3244, 3164 ($NH_2$), 2959, 2782 (alkyl), 1671 (C=O) $cm^{-1}$. $^1H$ NMR (DMSO): δ 4.82 (d, 3H, $CH_3$), 5.19 (d, 1H, J=10.2 Hz, CH), 5.83-5.96 (m, 1H, CH), 6.60 (s, 2H, $NH_2$), 7.8 (br, 1H, NH), 8.40 (s, 1H, N=CH), 9.23 (s, 1H, NH) $^{13}C$ NMR (DMSO): δ 47.1, 105.4, 117.9, 130.3, 146.5, 149.4, 154.2, 157, 186.9. LC-MS: m/z 283 ($M^{+1}$).

EXAMPLE 5

Synthesis of (7-Imino-3-phenyl-2-thioxo-3,7-dihydro-2H-thiazolo[4,5-d]pyrimidin-6-yl)-urea (19)

A mixture of 4-(Ethoxymethylene)-amino-3-(phenyl)-2-thioxo-1,3-thiazole-5-carbonitrile 12 (8 g, 28.8 mmol), semicarbazide hydrochloride (3.2 g, 28.8 mmol) and triethyl amine (14 ml) in absolute ethanol (80 ml) was stirred at 22° C. for 10 hrs. The appeared precipitate was filtered and washed with absolute ethanol (60 ml) and water (40 ml) to give pure compound. 19 (6.5 g) and purity of compound was confirmed by HPLC.

Yield: 85%. (HPLC purity 99%) White solid; mp: 225° C. IR (KBr), 3245, 3162 ($NH_2$), 2959, 2786 (alkyl), 1678 (C=O) $cm^{-1}$. $^1H$ NMR (DMSO): δ 6.37 (s, 2H, $NH_2$), 7.38-7.58 (m, 5H, Ar), 8.22 (s, 1H, N=CH), 8.47 (br, 1H, NH), 9.73 (s, 1H, NH), $^{13}C$ NMR (DMSO): δ 98.3, 128.7, 129.3, 131.3, 133.8, 135.7, 155.9, 158.5, 159.1, 164, 191.7, LC-MS: m/z 319 ($M^{+1}$).

EXAMPLE 6

Synthesis of (3-p-iodophenyl-7-imino-2-thioxo-3,7-dihydro-2H-thiazolo[4,5-d]pyrimidin-6-yl)-urea (20)

A mixture, of 4-(Ethoxymethylene)-amino-3-(p-iodophenyl)-2-thioxo-1,3-thiazole-5-carbonitrile 13 (4 g, 10 mmol), semicarbazide hydrochloride (1.2 g, 10 mmol) and triethyl amine (5 ml) in absolute ethanol (45 ml) was stirred at 20° C. for 12 hrs. The appeared precipitate was filtered and washed with absolute ethanol (50 ml) and water (40 ml) to give pure target compound. 20 (2.7 g) and purity of compound was confirmed by HPLC.

Yield: 68%, purity 99%(HPLC), White solid; mp: 235° C. IR (KBr), 3249, 3163 ($NH_2$), 1673 (C=O). $cm^{-1}$
$^1H$ NMR (DMSO): δ 6.37 (s, 2H, $NH_2$), 7.23 (d, 2H, J=8.7 Hz, Ar), 7.94 (d, 2H, J=8.7 Hz, Ar), 8.47 (s, 1H, NH), 9.75 (s, 1H, NH), $^{13}C$ NMR (DMSO): δ 98.3, 128.8, 129, 131, 133.8, 136, 156, 158.5, 159.1, 164, 191, LC-MS: m/z 443 ($M^+$), 444 ($M^{+1}$).

EXAMPLE 7

Synthesis of (3-Benzyl-7-imino-2-thioxo-3,7-dihydro-2H-thiazolo[4,5-d]pyrimidin-6-yl)-urea (21)

A mixture of (3-Benzyl-7-imino-2-thioxo-3,7-dihydro-2H-thiazolo[4,5-d]pyrimidin-6-yl)-urea 14 (6 g, 20.6 mmol), semicarbazide hydrochloride (2.3 g, 20.6 mmol) and triethyl amine (12 ml) in absolute ethanol (60 ml) was stirred at 26° C. for 18 hrs. The appeared precipitate was filtered and washed with absolute ethanol (60 ml) and water (50 ml) to give pure target compound. 21 (4.5 g) and Purity of compound was confirmed by HPLC.

Yield: 75%. (HPLC purity 100%), White solid; mp: 190° C. IR (KBr), 3249, 3165 ($NH_2$), 1674 (C=O) $cm^{-1}$
$^1H$ NMR (DMSO): δ 5.46 (s, 2H, $CH_2$), 6.60 (s, 2H, $NH_2$), 7.06-7.31 (m, 5H, Ar) 8.18 (s, 1H, N=CH), 9.24 (br, 1H, NH), $^{13}C$ NMR (DMSO): δ 52, 98.3, 128.7, 129.3, 131.4, 133.7, 158.5, 158.8, 159.1, 159.4, 164, 191.8 LC-MS: m/z 332 ($M^+$), 333 ($M^{+11}$).

EXAMPLE 8

Synthesis of Furan-2-carboxylic acid (3-ethyl-7-imino-2-thioxo-3,7-dihydro-2H-thiazolo[4,5-d]pyrimidin-6-yl)-amide (22)

A mixture of 4-(Ethoxymethylene)-amino-3-(ethyl)-2-thioxo-1,3-thiazole-5-carbonitrile 8 (12 g, 52.4 mmol), furoic acid hydrazide (6.6 g, 52.4 mmol) and triethyl amine (26 ml) in absolute ethanol (112 ml) was stirred at 24° C. for 19 hrs. The appeared precipitate was filtered and washed with absolute ethanol (108 ml) and water (50 ml) to give pure compound 22 (12.4 g) and Purity of compound was confirmed by HPLC.

Yield: 95%. 95%, (HPLC purity 100%), White solid; mp: 226° C. IR (KBr), 3376 (NH), 2966, 2946 (alkyl), 1673 (C=O) $cm^{-1}$. $^1H$ NMR ($CDCl_3$): δ 1.27 (t, 3H, J=7.2 Hz, $CH_3$), 4.36 (q, 2H, J=7.2 Hz, $CH_2$), 6.50 (q, 1H, J=1.7 Hz, furan), 6.91 (d, 1H, J=2.7 Hz), 7.67 (s, 1H, furan), 8.24 (br, 1H, NH), 8.74 (s, 1H, N=CH), 9.42 (br, 1H, NH). $^{13}C$ NMR (DMSO): δ 13.9, 48.2, 100.9, 110, 111, 127.5, 127.7, 128.5, 135.0, 154.3, 163.0, 187.4. LC-MS: m/z 321 ($M^+$).

EXAMPLE 9

Synthesis of Furan-2-carboxylic acid (7-imino-3-propyl-2-thioxo-3,7-dihydro-2H-thiazolo[4,5-d]pyrimidin-6-yl)-amide (23)

A mixture of 4-(Ethoxymethylene)-amino-3-(-propyl)-2-thioxo-1,3-thiazole-5-carbonitrile 9 (9 g, 37 mmol), furoic acid hydrazide (4.7 g, 37 mmol) and triethyl amine (16 ml) in absolute ethanol (75 ml) was stirred at 24° C. for 6 hrs. The appeared precipitate was filtered and washed with absolute ethanol (84 ml) and water (52 ml) to give pure compound 23 (8 g) and purity of compound was confirmed By HPLC.

Yield: 92%. (HPLC purity 100%), White solid; mp: 206° C. IR (KBr), 3376 (NH), 2964, 2946 (alkyl), 1672 (C=O) $cm^{-1}$. $^1H$ NMR ($CDCl_3$): δ 0.92 (t, 3H, J=6.9, $CH_3$), 1.76 (m, 2H, $CH_2$), 4.28 (t, 2H, J=6.9 Hz, $CH_2$). 6.53 (q, 1H, furan), 6.93 (d, 1H, furan), 7.69 (s, 1H, furan), 8.29 (br, 1H, NH), 8.77 (s, 1H, N=CH), 9.48 (br, 1H, NH). LC-MS: m/z 335 ($M^+$), 356 ($M^{+1}$).

EXAMPLE 10

Synthesis of Furan-2-carboxylic acid (3-butyl-7-imino-2-thioxo-3,7-dihydro-2H-thiazolo[4,5-d]pyrimidin-6-yl)-amide (24)

A mixture of 4-(Ethoxymethylene)-amino-3-(butyl)-2-thioxo-1,3-thiazole-5-carbonitrile 10 (8 g, 31 mmol), furoic acid hydrazide (4 g, 31 mmol) and triethyl amine (16 ml) in absolute ethanol (75 ml) was stirred at 25° C. for 8 hrs. The appeared precipitate was filtered and washed with absolute ethanol (65 ml) and water (45 ml) to give pure compound 24 (6.6 g) and Purity of compound was confirmed by HPLC.

Yield: 86%. (HPLC purity 100%), White solid; mp: 210° C. IR (KBr), 3375 (NH), 2873, 2961 (alkyl), 1674 (C=O) $cm^{-1}$. $^1H$ NMR ($CDCl_3$): δ 0.89 (t, 3H, J=7.2, $CH_3$). 1.33 (q, 2H, J=7.2 Hz, CH2), 1.69-1.71 (m, 2H, $CH_2$), 4.30 (t, 2H, J=7.2 Hz, $CH_2$), 6.50 (q, 1H, furan), 6.91 (d, 1H, furan), 7.67 (s, 1H, furan), 8.24 (br, 1H, NH), 8.72 (s, 1H, NH), 9.44 (br, 1H, NH). $^{13}C$ NMR ($DMSOd_6$): δ13.5, 19.4, 28.6, 45.4, 100.9, 110.9, 111.6, 143.1, 147.5, 151.5, 151.9, 153.4, 163.8, 188.9, LC-MS: m/z 349 ($M^+$), 350 ($M^{+1}$).

EXAMPLE 11

Synthesis of Furan-2-carboxylic acid (7-imino-3-propenyl-2-thioxo-3,7-dihydro-2H-thiazolo[4,5-d]pyrimidin-6-yl)-amide (25)

A mixture of 4-(Ethoxymethylene)-amino-3-(allyl)-2-thioxo-1,3-thiazole-5-carbonitrile 11 (12 g, 49.8 mmol), furoic acid hydrazide (6.3 g, 49.8 mmol) and triethyl amine (24 ml) in absolute ethanol (116 ml) was stirred at 21° C. for 12 hrs. The appeared precipitate was filtered and washed with absolute ethanol (125 ml) and water (108 ml) to give pure compound 25 (11 g) and Purity of compound was confirmed By HPLC.

Yield: 94%. (HPLC purity 100%), White solid; mp: 218° C. IR (KBr), 3377 (NH), 2964, 2946 (alkyl), 1673 (C=O) $cm^{-1}$. $^1H$ MR ($CDCl_3$): δ 4.98 (d, 3H, $CH_3$), 5.14 (d, 1H, J=10.2 Hz, CH), 5.89-5.98 (m, 1H, CH) 6.53 (q, 1H, J=1.5 Hz, furan), 6.94 (d, 1H, J=3 Hz, furan), 7.69 (s, 1H, furan), 8.87 (s, 1H, N=CH), 9.86 (s, 1H, NH). $^{13}C$ NMR ($DMSOd_6$): δ 47.3, 100.9, 110.9, 111.6, 118.1, 129.8, 143.1, 147.5, 151, 152, 153, 163, 166.9, LC-MS: m/z 333 ($M^+$), 334 ($M^{+1}$).

EXAMPLE 12

Synthesis of Furan-2-carboxylic acid (7-imino-3-phenyl-2-thioxo-3,7-dihydro-2H-thiazolo[4,5-d]pyrimidin-6-yl)-amide (26)

A mixture of 4-(Ethoxymethylene)-amino-3-(phenyl)-2-thioxo-1,3-thiazole-5-carbonitrile 12 (8 g, 29 mmol), furoic acid hydrazide (3.6 g, 29 mmol) and triethyl amine (14 ml) in absolute ethanol (116 ml) was stirred at 24° C. for 14. The appeared precipitate was filtered and washed with absolute ethanol (88 ml) and water (54 ml) to give pure compound 26 (7 g) and Purity of compound was confirmed By HPLC.

Yield: 88%. White solid; mp: 228° C. IR (KBr), 3376 (NH), 2964, 2946 (alkyl), 1672 (C=O) $cm^{-1}$. $^1H$ NMR ($CDCl_3$): δ 6.78 (q, 1H, furan), 7.39 (d, 1H, furan), 7.59-7.65 (m, 6H, Ar including furan.), 8.01 (s, 1H, N=CH), 9.71 (s, 1H, NH). $^{13}C$ NMR ($DMSOd_6$): δ100, 111, 112, 143.2, 147, 128.8, 129.3, 131, 135, 156, 158, 159.1, 164, 192, LC-MS: m/z 369 ($M^+$), 370 ($M^{+1}$).

Pharmacological activity of compound of the invention was determined by the following in vitro assay to evaluate $A_{2A}$ receptor antagonist activity.

In Vitro Radioligand Binding Assays
Procedure
Membrane Preparations

About $1 \times 10^6$ cells per ml of HEK 293 cells (stably expressing human $A_{2A}R$ and $A_1R$, were centrifuged at 2,500 rpm for 2 minutes in 15 ml centrifuge tubes. Cells were washed twice with ice-cold PBS (pH 7.4). Pellet of washed cells was resuspended in hypotonic lysis buffer (10 mM NaCl, 2 mM MgCl2, 1 mM DTT, 10 mM Hepes; 2 mM PMSF, pH 7.4) and sonicated (4 cycles of 10 s duration each). Homogenate were centrifuged at 2,500 rpm for 10 minutes at 4° C. Resulting supernatants was again centrifuged at 38,000 rpm for 30 minutes at 4° C. Pellets obtained was resuspended in Tris-HCl (pH 7.4) buffer. Membrane protein concentrations were determined using Lowry reagent method (Lowry et al., 1951) and absorbance was read at 660 nm using UV/Vis. spectrophotometer. Aliquots of membrane proteins from both $A_{2A}R$ and $A_1R$ were rapidly frozen and stored at −20° C.

Radioligand Binding Assay

Radioligand [$^3$H] ZM 241385 was a kind gift from Dr. Surendra Gupta (president, American Radiolabeled Chemicals, St. Louis, USA) and [$^3$H] DPCPX was purchased from American Radiolabeled Chemicals, St. Louis, USA.

Saturation Binding Assay for [$^3$H] ZM241385 and [$^3$H] DPCPX

Saturation binding analysis was carried out to determine two important parameters; $K_D$ (equilibrium dissociation constant) and $B_{max}$ (receptor density) (Bylund and Yamamura, 1990). $K_D$ is defined as the concentration of ligand that will occupy 50% of the receptors. $K_D$ value can be used to calculate the concentration of radiolabelled ligand required to occupy a desired proportion of receptors. $B_{max}$ is the maximum density of receptors. This is usually corrected using the amount of protein present in the binding assay and expressed as amount of ligand bound/mg protein.

[$^3$H] ZM 241385 (standard $A_{2A}$ antagonist) has been used to evaluate $K_D$ and $B_{max}$ values for human and rat $A_{2A}R$. Similarly, [$^3$] DPCPX (standard $A_1$ antagonist) has been used to determine $K_i$ and $B_{max}$ values for human and rat $A_1R$.

About 10 μg of membrane protein was added to each well of multiscreen 96-well plate equipped with GF/B filters. Incubation buffer (50 mM Tris, 1 mM EDTA, pH 7.4) containing adenosine deaminase (1 U/ml) was added to each well to remove endogenous adenosine bound to the receptors and volume was adjusted to 100 μl by adding incubation buffer. Plate was incubated at 37° C. for 1 hour. Varying concentrations (0.125, 0.25, 0.5, 1, 2, 3, 4, 5, 6, 7 and 8 nM for [$^3$H] ZM 241385 and 0.1, 4, 6, 8, 10, 12, 14 and 16 nM for [$^3$H] DPCPX) were added to respective wells in triplicates. Final volume was adjusted to 200 μl by adding incubation buffer and incubated at 26° C. for 30 minutes. Binding reaction was terminated by rapid filteration of filter plates using vacuum manifold system. Filterate (unbound radioligand) was collected in a 96-well plate laying down the filter plate. Filters were washed three times with ice-cold washing buffer (50 mM Tris-Cl; 2.5 mM MgCl$_2$ pH 7.4). Finally, 100 μl of scintillation fluid was added to all wells of plate containing unbound filtrate as well as to the filter plate (bound radioligand) and incubated overnight at room temperature. Non-specific binding (binding of a ligand at non-specific sites, other than ligand-binding sites of receptor) was determined by adding 50 μM of NECA (for [3H] ZM 241385) and 50 μM of CPA (for [$^3$H] DPCPX). β-counts emitted by [$^3$H] ZM 241385 and [$^3$H] DPCPX were read using β-counter.

Competitive Binding Assay

To evaluate the binding affinity of standard ($A_{2A}R$ antagonist SCH 58261 and agonist NECA) and synthesized compounds 15-26 displacement/competitive-binding assays were performed. About 10 μg of membrane protein was added to each well of a 96-well filter plate. Incubation buffer containing adenosine deaminase (1 U/ml) was added to the membrane protein and incubated at 37° C. for 1 hour, to remove endogenous adenosine. Varying concentrations (1 pM to 1 μM) of test compounds 15-26 were added in duplicate and volume was adjusted to 50 μl by adding incubation buffer.

Further, constant concentration of radioligands (1 nM for [$^3$H] ZM 241385 and 0.75 nM of [$^3$H] DPCPX) was added to respective wells and final volume was adjusted to 200 μl by adding the incubation buffer. Filter plates were incubated at 26° C. for 30 minutes and reaction was terminated by rapid filtration of unbound radioligands. Filters containing ligand bound receptors were washed three times with ice-cold washing buffer to completely remove any unbound radioligand or receptor. Finally, 100 μl of scintillation fluid was added to each well and incubated overnight at room temperature. β-counts emitted from bound radioligands ([$^3$H] ZM241385 and [$^3$H] DPCPX) were counted using β-counter. Duplicate values of β-counts per minute at corresponding concentrations (1 pM to 1 μM) were added to the data sheet of graph pad prism 4.0. Concentration values were considered as X-values and counts per minute were considered as Y-values (in duplicate). X-values were transformed into logX and $K_i$ value was calculated using nonlinear regression (curve fit program). The calculated $K_i$ values for $A_{2A}R$ and $A_1R$ are given bellow (Table 1)

TABLE 1

Radioligand binding assay result of thiazolopyrimidine compounds (15-26).

| Compound no | hA$_{2A}$ binding Ki ± SD$^a$ (nM) | hA$_1$ binding Ki ± SD$^b$ (nM) | hA$_1$/hA$_{2A}$ ratio |
|---|---|---|---|
| 15. | 0.09 ± 0.01 | 0.00016 ± 0.007 | 0.00177 |
| 16. | 0.0038 ± 0.001 | 2.8 ± 0.8 | 736.84 |
| 17. | 0.089 ± 0.01 | 1.04 ± 0.84 | 11.685 |
| 18. | 0.092 ± 0.01 | 0.47 ± 0.1 | 5.11 |
| 19. | 0.063 ± 0.008 | 1.5 ± 1.10 | 23.81 |
| 20. | 0.017 ±0.01 | 2.5 ± 1.1 | 147.06 |
| 21. | 0.023 ± 0.014 | 0.14 ± 0.086 | 6.09 |
| 22. | 1.2 ± 1.10 | 0.016 ± 0.01 | 0.0133 |
| 23. | 0.024 ± 0.01 | 0.087 ± 0.05 | 3.625 |
| 24. | 0.029 ± 0.01 | 0.0053 ± 0.001 | 0.183 |
| 25. | 0.17 ± 0.1 | 0.59 ± 0.11 | 3.47 |
| 26. | 0.33 ± 0.75 | 0.0085 ± 0.001 | 0.026 |
| SCH58261 | 1.23 | 594.1 | 483 |

The result of $A_{2A}R$ binding assay are expressed as inhibition constants ($K_i$ in nM). The $A_1R/A_{2A}R$ describes their selectivity over $A_1R$. In the set of thiazolopyrimidine urea derivatives (15-21), ethyl substitution (15) exhibited significantly higher binding affinity with $A_1$ receptor (0.00016±0.007 nM) as compared to $A_{2A}R$ (0.09±0.01 nM). Homologation of one carbon in compound 15 gave the propyl derivative of thiazolo pyrimidine urea (16). The binding affinity of 16 with $A_{2A}R$ was significantly improved with very high selectivity for the receptor (766-fold selectivity over $A_1$ adenosine receptor), and was better than the known antagonist SCH 58261 (Ki=1.23±0.016, hA$_1$/hA$_2$=483). However 3-carbon chain with π-overlap in allyl derivative (18) displayed good binding affinity (Ki=0.092±0.01) but reduced selectivity (hA$_1$/hA$_2$=5.11). Further extending the alkyl chain to give butyl derivative of thiazolo-pyrimidine urea (17) resulted in decreased selectivity over $A_1$ receptor. Incorporation of aromatic ring (phenyl) in thiazolopyrimidine urea (19) showed enhanced binding affinity and selectivity, however. p-iodophenyl substitution (20) on the pharmacophore gave extremely superior binding affinity and selectivity (144 fold). Insertion of one carbon homologation in planer aromatic ring in thiazolopyrimidine urea (21) led decreased selectivity. Hence, it can be concluded that both 19 and 20 possessed promising activity, yet the compound (16) is most active among all thiazolopyrimidine urea derivatives.

The amino ($NH_2$) group of urea moiety of thiazolo-pyrimidine pharmacophore was replaced by furan ring to give another set of compounds (22-26). Overall substituent effects to binding affinity (propyl>butyl>allyl>aryl>ethyl) and selectivity (propyl>allyl>butyl>aryl>ethyl) profile of thiazolopyrimidine furanamide (22-26) decreased, however in the set of compound (22-26) propyl derivative (23) showed maximum binding and selectivity to $A_{2A}R$. The finding clearly demonstrated that bicyclic thiazolo-pyrimidine urea derivatives (15-21) were more potent and selective than the corresponding bicyclic thiazolo-pyrimidine furonamide derivatives (22-26).

cAMP Functional Assay

Procedure

To determine the modulation in cAMP concentrations, cells were pre-treated with Forskolin. Forskolin is commonly used to activate adenylyl cyclase, so as to raise the levels of cAMP, in the various cell physiology experiments. About $1 \times 10^6$ of HEK 293 cells were treated with 25 µM of Forskolin at 37° C. for 2 hours in the $CO_2$ incubator, followed by 100 nM concentrations of $A_{2A}R$ agonist (NECA), antagonists (SCH 58261) and synthesized compound (15-26) for 24 h. Cells were washed with ice-cold PBS (pH 7.4). Further, cells were treated with 0.1M HCl, incubated for 10 minutes and visually inspected to verify cell lysis. Lysed cells were centrifuged at 1000 rpm at room temperature and the supernatant was used directly for cAMP assay using direct cAMP assay kit. All standards and samples were run in duplicate. 50 µl of the neutralizing reagent was added into each well of 96-well microplate coated with goat anti-rabbit IgG antibody, except the total activity (TA) and blank wells. Again, 100 µl of HCl (0.1M) was added into the NSB (Non-specific bound) and the Bo (0 pmol/ml standard) Wells: 100 µl of standards 1 to 5 was pippeted into the appropriate wells. 50 µl of 0.1M HCl was added into the NSB wells, followed by 50 µl of blue conjugate (alkaline phosphatase conjugated with cAMP) into each well except the TA and blank wells. 50 µl of yellow coloured primary antibody against cAMP into each well, except the blank, TA and NSB wells. Microplate was incubated at room temperature for 2 hours on a plate shaker. Wells were washed twice with 400 µl of wash solution. 5 µl of blue conjugate was added to the TA wells, followed by the addition of 200 µl of p-nitrophenyl phosphate substrate solution to every well. Plate was again incubated for 1 hour without shaking. Reaction was stopped by adding 50 µl of stop solution to every well. Optical density was read at 405 nm with correction between 570 and 590 nm.

The average net O.D. bound for each standard and sample was calculated using formula;

Average Net OD=Average bound OD−Average NSB OD

The binding of each pair of standard wells as a percentage of the maximum binding well (Bo) was calculated using the formula;

Percent Bound=Net OD/Net Bo OD×100

Standard curve was prepared using Logit-Log Paper plot by drawing percent bound (B/Bo) versus concentration of cAMP for the standards. The concentration of the cAMP in the samples was determined by interpolation.

Statistical Analysis

Binding parameters were estimated by the computerized non-linear fitting program Graph Pad (Prism 4.0). Calculations were made according to Cheng and Prusoff (1973). Data were expressed as geometric means with 95% confidence limits in parentheses. Estimation of cAMP concentrations in functional assay was carried by Student's paired t-test. P<0.05 was considered significant. All analysis was performed by using GraphPad Prism 4.0 (GraphPad Software, San Diego, USA). Results are given, as mean±S.E.M

TABLE 2

| RESULTS OF cAMP FUNCTIONAL ASSAY | |
|---|---|
| Compound no | cAMP (nM) |
| 15. | 0.085 |
| 16. | 0.14 |
| 17. | 0.083 |
| 18. | 0.08 |
| 19. | 0.078 |
| 20. | 0.076 |
| 21. | 0.067 |
| 22. | 0.12 |
| 23. | 0.092 |
| 24. | 0.06 |
| 25. | 0.084 |
| 26. | 0.048 |
| SCH58261 | 0.25 |
| NECA | 0.40 |

All synthesized compound significantly decreased cAMP concentration as compared to NECA ($A_{2A}$ agonist) and result indicate that all compound have very good $A_{2A}$ receptor antagonist capability. cAMP concentration for SCH 58261 is 0.25 nM. cAMP concentration in all the compounds (15-26) was lower than known antagonist SCH58261 (Table 2). The results demonstrated that the compounds 15-26 possessed great potential as $A_{2A}$ receptor antagonists.

We claim:
1. A compound of formula 1,

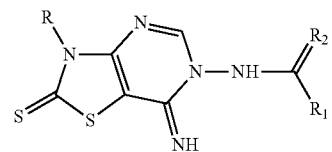

Formula 1 wherein R is selected from the group consisting of hydrogen, alkyl having up to 10 carbon atoms, allyl, cycloalkyl, benzyl, an aromatic optionally substituted with halogen, OH, COOH, $OCH_3$, or alkyl, pyridyl, piperidine, piperazine, and morphine, $R_1$ is selected from the group consisting of $NH_2$, NHR', and $N(R')_2$ where R' is aliphatic or olefinic and has up to 10 carbon atoms, a heterocycle selected from the group consisting of furan, thiophene, pyrrole, pyridyl, piperazine and morphine, and $R_2$ is O or S.

2. The compound as claimed in claim 1, represented by formula 1a

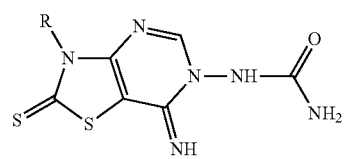

Formula 1a wherein R is selected from the group consisting of ethyl, propyl, allyl, butyl, phenyl, benzyl, and p-iodo phenyl.

3. The compound as claimed in claim 1 represented by Formula 1b

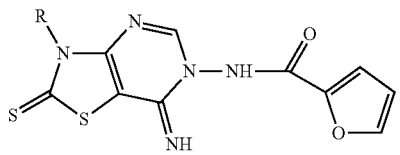

Formula 1b wherein R is selected from the group consisting of ethyl, propyl, allyl, butyl, and phenyl.

4. The compound as claimed in claim 1, wherein the compound of formula 1 is selected from the group consisting of:
  a) (3-Ethyl-7-imino-2-thioxo-3,7-dihydro-2H-thiazolo[4,5-d]pyrimidin-6-yl)-urea (15),
  b) (7-Imino-3-propyl-2-thioxo-3,7-dihydro-2H-thiazolo[4,5-d]pyrimidin-6-yl)-urea (16),
  c) (7-Imino-3-butyl-2-thioxo-3,7-dihydro-2H-thiazolo[4,5-d]pyrimidin-6-yl)-urea (17),
  d) (7-Imino-3-allyl-2-thioxo-3,7-dihydro-2H-thiazolo[4,5-d]pyrimidin-yl)-urea (18),
  e) (7-Imino-3-phenyl-2-thioxo-3,5-dihydro-2H-thiazolo[4,5-d]pyrimidin-6-yl)-urea (19),
  f) (3-p-iodophenyl-7-imino-2-thioxo-3,7-dihydro-2H-thiazolo[4,5-d]pyrimidin-6-yl)-urea (20),
  g) (3-Benzyl-7-imino-2-thioxo-3,7-dihydro-2H-thiazolo[4,5-d]pyrimidin-6-yl)-urea (21),
  h) Furan-2-carboxylic acid (3-ethyl-7-imino-2-thioxo-3,7-dihydro-2H-thiazolo[4,5-d]pyrimidin-6-yl)-amide (22),
  i) Furan-2-carboxylic acid(7-imino-3-propyl-2-thioxo-3,7-dihydro-2H-thiazolo[4,5-d]pyrimidin-6-yl)-amide (23),
  j) Furan-2-carboxylic acid(3-butyl-7-imino-2-thioxo-3,7-dihydro-2H-thiazolo[4,5-d]pyrimidin-6-yl)-amide (24),
  k) Furan-2-carboxylic acid(7-imino-3-propenyl-2-thioxo-3,7-dihydro-2H-thiazolo[4,5-d]pyrimidin-6-yl)-amide (25), and
  l) Furan-2-carboxylic acid(7-imino-3-phenyl-2-thioxo-3,7-dihydro-2H-thiazolo[4,5-d]pyrimidin-6-yl)amide (26).

5. A process for inhibiting receptor activity of an $A_{2A}$ subtype adenosine receptor in a subject, the process comprising administering to the subject the compound as claimed in claim 1.

6. The method as claimed in claim 5, wherein the compound has Adenosine $A_{2A}$ receptor affinity in the range of 0.0038-1.2 nM.

7. The method as claimed in claim 5, wherein the compound has Adenosine $A_{2A}$ receptor antagonistic ability in the range of 0.048-0.14 nM cAMP concentration.

8. A process for preparation of 3-substituted (7-imino-2-thioxo-3,7-dihydro-2H-thiazolo[4,5-d]pyrimidin-6-yl-amide, where the process steps comprises
  a) reacting imino ether derivatives of general formula A

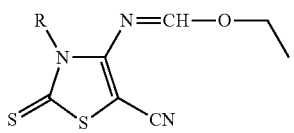

A wherein R is selected from a group consisting of, ethyl, propyl, allyl, butyl, phenyl, benzyl, and p-iodo phenyl with acid hydrazide in alcoholic solvent in presence of a basic catalyst selected from the group consisting of amine, KOH, and NaOH, at a temperature ranging between 20-32° C. for a period ranging between 6-20 hours to obtain precipitated compound, and
  b) filtering the precipitated compound obtained in step (a), followed by washing with ethanol/water to obtain the 3-substituted (7-imino-2-thioxo-3,7-dihydro-2H-thiazolo[4,5-d]pyrimidin-6-yl-amide.

9. The process as claimed in claim 8, wherein the acid hydrazide is selected from the group consisting of semicarbazide, furoic acid hydrazide hydrazide, thiophene-2-carboxylic acid hydrazide, benzoic acid hydrazide, iso-nicotinic acid hydrazide, pyrimidine-4-carboxylic acid hydrazide, and triazole-4-carboxylic acid hydrazide.

10. The process as claimed in claim 8, wherein the alcoholic solvent is selected from the group consisting of ethanol, methanol, propanol, iso-propanol, butanol, and a mixture thereof.

* * * * *